United States Patent [19]

Necker et al.

[11] 4,186,306
[45] Jan. 29, 1980

[54] PERLITE EXPANSION DENSITY CONTROL SYSTEM

[75] Inventors: Carl G. Necker, Littleton; Richard R. Colwell, Englewood, both of Colo.

[73] Assignee: Johns-Manville Corporation, Denver, Colo.

[21] Appl. No.: 856,821

[22] Filed: Dec. 2, 1977

[51] Int. Cl.² .......................................... G01M 23/00
[52] U.S. Cl. ................................ 250/360; 250/432 R; 250/433
[58] Field of Search ............... 250/360, 359 R, 432 R, 250/433; 318/340

[56] References Cited

U.S. PATENT DOCUMENTS

| | | | |
|---|---|---|---|
| 2,979,649 | 4/1961 | Leighton | 318/480 |
| 4,044,259 | 8/1977 | Wyton et al. | 250/360 |

OTHER PUBLICATIONS

"Use Radioactive Instruments", Stewart et al., Control Eng., Mar. 1955, pp. 50-56.

"Encyclopedia of Instrumentation and Control", Considine, 1971, pp. 191-193, 685-689, and 744.

Primary Examiner—Bruce C. Anderson
Attorney, Agent, or Firm—Robert M. Krone; Joseph J. Kelly; James W. McClain

[57] ABSTRACT

A perlite expander control system is disclosed in which a source of and detector for penetrating radiation are used to determine the density of an expanded perlite product flowing through a conduit. The density of the perlite product will be inversely proportional to the amount of penetrating radiation transmitted to the detector. A signal generated by the detector in response to the amount of transmitted radiation received is processed in appropriate circuitry to control the feed of raw perlite ore to the expander, thus resulting in the correct amount of ore being fed to the expander per unit time to result in obtaining the desired degree of perlite expansion. Typically beta, gamma or X radiation of various energies may be used as the penetrating radiation.

7 Claims, 1 Drawing Figure

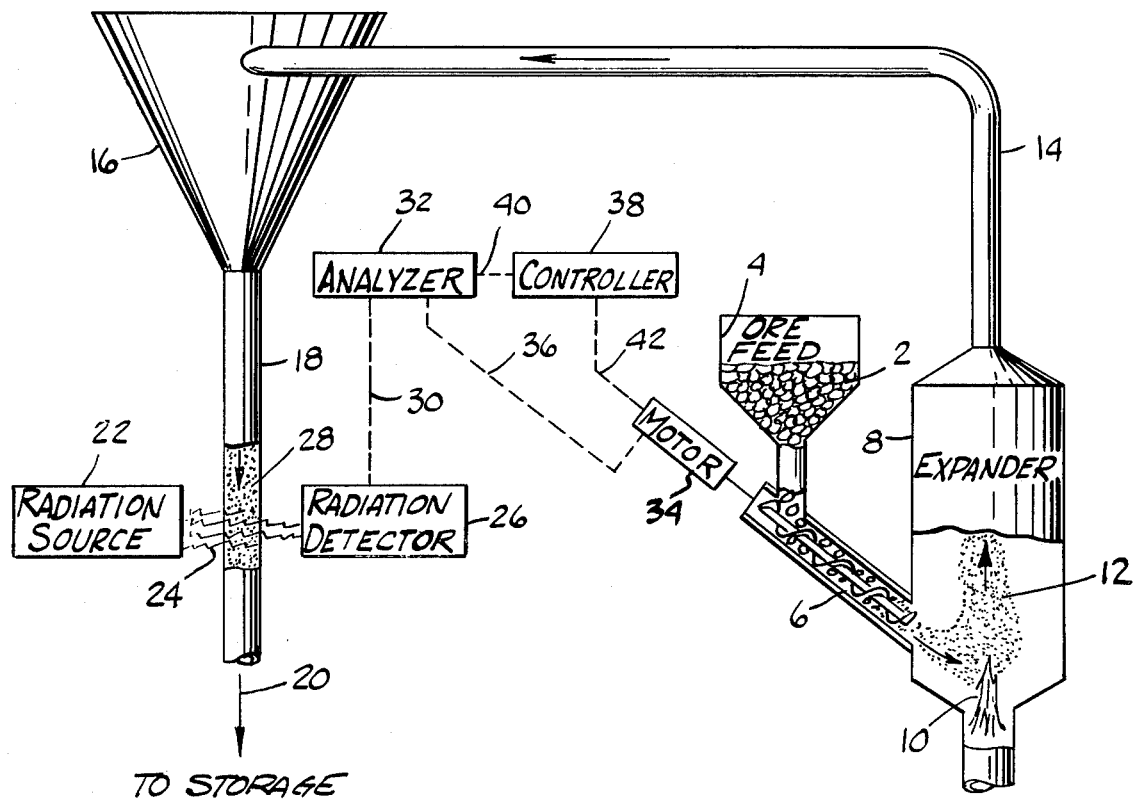

PERLITE EXPANSION DENSITY CONTROL SYSTEM

BACKGROUND OF THE INVENTION

The invention herein relates to a method for controlling the density of expanded perlite.

Perlite is a volcanic rock which contains small amounts of water within its structure. When perlite granules are rapidly heated to temperatures on the order of about 1800° F. the water turns to steam and the perlite granules "pop" or expand to a volume of 4 to 20 times the volume of the unexpanded granules, with an attendant decrease in the bulk (or "apparent") density of the perlite. In this expanded form the perlite has found many such uses, such as lightweight aggregate and as a noncombustible lightweight thermal insulation.

In many of the perlite use applications (such as insulating boards) substantial uniformity of perlite bulk density is important in order to obtain optimum end products. Consequently, it is imperative for the expanded perlite manufacturer to control closely the expansion process and to act promptly to correct any deviations in the product from the desired final density properties.

In the past it has been common practice to determine the bulk density of the perlite product by taking periodic samples from the collection bin where the expanded perlite is deposited. The density of these samples was determined by conventional density measurements. The results of these tests were then reported back to the expander operators and the operation of the expanders adjusted accordingly where deviations from the desired density were discovered. This procedure is obviously very time consuming and results in significant delays in the discovery of processing irregularities. This in turn can lead to the production of large quantities of unusable product during the period between testing intervals.

It would therefore be advantageous to have a system which would monitor the density of the expanded perlite on a substantially continuous basis. It would also be very advantageous to have a system in which the monitoring device would also generate appropriate signals to related equipment which would promptly alter the operation of the system so that the desired density could again be obtained while yet minimizing the amount of "off spec" material which would be produced before the system controls could be corrected.

SUMMARY OF THE INVENTION

The invention herein is a control system utilizing a radiation gauge and feedback equipment and circuitry which permits the density of expanded perlite to be continuously monitored and the expander feed system operation altered as necessary promptly to maintain the proper degree of perlite expansion and density reduction. In summary, the invention is an improved method of monitoring the expanded bulk density of expanded perlite in a perlite expansion process, which improvement comprises (a) passing the expanded perlite through a conduit section of predetermined volume; (b) impinging penetrating radiation on one side of the conduit section while the expanded perlite is passing therethrough; (c) detecting on the other side of the conduit section at least a portion of the unabsorbed fraction of the incident penetrating radiation which passes through the perlite and the conduit section; and (d) obtaining a signal proportional to the bulk density of the expanded perlite by means of a predetermined correlation among mass flow rate, conduit section volume and detected amount of the unabsorbed fraction of incident radiation.

The invention also comprises an improved method of monitoring the expanded bulk density of the expanded perlite and using the information from such monitoring to control the density of expanded perlite in a process for expanding perlite. The improvement comrises (a) passing the unexpanded perlite through a conduit section of predetermined volume; (b) impinging penetrating radiation on one side of the conduit section while the expanded perlite is passing therethrough; (c) detecting on the other side of the conduit section at least a portion of the unabsorbed fraction of the incident radiation which passes through the perlite and the conduit section; (d) obtaining a signal proportional to the bulk density of the expanded perlite by means of a predetermined correlation among mass flow rate, conduit section volume and detected amount of the unabsorbed fraction of incident radiation; and (e) utilizing the signal obtained to control the amount of unexpanded feed ore supplied to the perlite expander whereby the density of the expanded ore is maintained at the desired level.

BRIEF DESCRIPTION OF THE DRAWING

The single FIGURE of the drawing is a schematic diagram of the process of this invention.

DETAILED DESCRIPTION AND PREFERRED EMBODIMENTS

The process of this invention will be best understood by reference to the attached drawing.

In the process raw perlite ore 2 is fed from a storage hopper 4 into feed conveyor 6 (illustrated as a screw conveyor) which meters the unexpanded ore into the expander 8 where it falls into a high temperature flame 10 created by an oil or gas burner (not shown). During its short residence time in flame 10, the unexpanded ore is rapidly heated and the steam created by the included water causes the perlite to "pop" and form low density expanded perlite ore 12. This low density expanded perlite 12 is entrained in the flow of air and gas rising through the expander 8 and is carried out of the expander through a duct 14 to separation means 16 (illustrated here as a cyclone) in which the solid material from the expander (which includes low density expanded product as well as some high density unexpanded ore and fractured particles of perlite) is separated from the air/gas stream and withdrawn through conduit 18 to be sent to storage as indicated by arrow 20. The apparent or bulk density of the solid product 28 in conduit 18 is the property of interest in the present invention. Commercial "expanded perlite product" comprises a mix of expanded perlite, unexpanded ore, and broken fines. The predominant component in obtaining the desired low bulk density for the product 28 is the low density expanded perlite fraction. For use in thermal insulating board it is desirable that the bulk density of the expanded perlite product 28 be on the order of about 2.5 to 6 lbs/ft$^3$ (0.04 to 0.1 g/cm$^3$). The portion of the unexpanded ore which is converted to the expanded perlite fraction will be determined by various parameters of the operation of the expander 8, including the rate at which the ore is fed into the flame 10. If the rate of ore feed is too great, the fraction of the feed which can be expanded during the short residence time in the flame will be unduly small and the overall bulk density of the product will be high. On the other hand, if the feed rate of ore is too low, there may be more fines produced as the perlite fractures or the fraction of expanded perlite may become too great, resulting in a product which is too low in density.

As noted above, in the past the practice has been to sample the product after reaching storage, subject the samples to conventional density determinations, and then manually adjust the ore feed rate to compensate for any deviations from desired product density. This results in the possibility of prolonged periods between samplings when the system can be running improperly and making "off spec" product before corrections can be made.

In the improvement of the present invention, however, there is substantially constant monitoring of the density of the perlite product 28 and prompt feedback to permit automatic control of the ore feed rate to optimize the perlite expansion process. The location of the monitoring point is positioned relative to the expander such that any deviation in the desired density production results in only a minimum of "off spec" product being formed before a correction is automatically induced.

In the present invention there is used a source 22 of penetrating radiation 24, the radiation preferably being beta, gamma or X radiation. Since the conduit 18 is normally a metal pipe, other forms of radiation such as infrared, visible light, ultraviolet light or the like are not operable in the present invention. The penetrating radiation 24 is focused upon the conduit 18 and a fraction of the radiation passes through the conduit wells and the perlite product 28 flowing inside the conduit and exits on the far side of conduit 18 where it is detected by radiation detector 26. The type and energy of the penetrating radiation 24 should be chosen such that a significant fraction of the radiation passes completely through the conduit 18 and perlite product 28 to reach detector 26, but there should also be a significant fraction of the radiation which is absorbed by the perlite product 28. Since the absorption of the radiation 24 by the material of conduit 18 will remain constant, the variations in the amount of transmitted radiation detected by detector 26 will be dependent upon the fraction of radiation 24 absorbed by the perlite product 28 inside conduit 18. Unless both the amount of radiation 24 absorbed by perlite product 28 and the fraction of radiation 24 transmitted to detector 26 are significant quantities, variations in either will be too small to allow effective control of the system. Those skilled in the art will be readily able to determine the correct type and energy of radiation 24 to be used considering the materials and size of conduit 18 as well as the amount of perlite product 28 within conduit 18 at any given time. For instance, a large thick-wall conduit 18 through which pass large unit quantities of perlite product 28 would probably not work effectively if the penetrating radiation 24 chosen consisted of low energy beta particles, since too few of them would be able to penetrate the conduit and perlite to be detected by detector 26. On the other hand, a small thin-wall conduit containing small amounts of perlite would probably not work effectively with high energy gamma rays used as the penetrating radiation 24, for so little of the radiation would be absorbed by the conduit and the perlite that the detector 26 would not be able to detect the changes in absorption caused by varying densities of the perlite.

The description of suitable radiation sources 22 and detectors 26 and guidelines for the proper choice of the type of penetrating radiation 24 will be found in a variety of references, including D. M. Considine, *Encylopedia of Instrumentation and Control* (1971); R. C. McMaster, *Non-Destructive Testing Handbook* (1959), Section 18; and P. J. Stewart et al, *Control Engineering* (March, 1955) pages 50-56.

While radiation sources and detectors have been used in the past to monitor and gauge thickness or density of solid substantially homogeneous items or density of flowing liquids, they have not to our knowledge ever been used to determine and monitor the density of loose granular materials such as the perlite product 28 which are entrained in a gas stream. The operation of the present invention is based on the principle that radiation absorption will be less for the lower density materials because their mass is spread out over a greater volume and therefore there will be less mass per unit volume passing through the fixed volume swept by the radiation beam as it tranverses conduit 18. Consequently, the lower the density the less radiation that will be absorbed per unit volume and the greater will be the fraction transmitted for detection by detector 26. Conversely, the higher the density of the perlite product 28, the less radiation will be transmitted to detector 26. The detection system must of course be calibrated for the particular installation, but once calibrated for a given conduit 18 only periodic calibration checks should be necessary since the volume within the conduit 18 through which the radiation is transmitted will not vary except by the small increments due to normal erosion of the inside of the conduit from the moving perlite. Initial calibration will also include determination of the correlation among perlite density, conduit volume, and radiation transmitted, using perlite samples of known density. This calibration will generally have to be redetermined if there is a significant change in the nature of the perlite ore feed. Periodic recalibration may also be required to compensate for prolonged decay of the radation source.

The output of detector 26 will be a signal which varies in strength proportionally to the amount of transmitted radiation received by the detector 26. This signal is transmitted through line 30 to analyzer 32. Analyzer 32 also receives signals from motor 34 through line 36 which indicate the rate at which motor 34 is driving conveyor 6, which is proportional to the rate at which the ore 2 is being fed into expander 8. If the density of the perlite product 28 is within the desired range, the analyzer 32 will recognize this by the strength of the signal from detector 26 and will not order any corrections in the speed of motor 34. However, if the amount of transmitted radiation detected by detector 26 is either too high or too low, the signal to analyzer 32 will be recognized as indicating a deviation from the desired density and the analyzer will send an appropriate signal to controller 38 through line 40 to increase or decrease the speed of motor 34 as required. Controller 38 will in turn send such a signal to motor 34 through line 42 and the rate of perlite ore feed to expander 8 will be adjusted appropriately. Typical circuitry and functioning of equipment to achieve this result is shown in the Considine and Stewart et al references mentioned above. It would be appropriate to have a conventional time delay function in the circuitry such that normal statistical variations in the density of perlite product 28 and its flow rate through the radiation beam in conduit 18 do not trigger constant and unnecessary minor adjustments in the speed of motor 34. Such a time delay function (such as appropriate capacitor circuits) will allow the control function of the system of the present invention to operate on the longer duration and more significant variations in perlite density, effectively screening out the minor and insignificant statistical short term variations.

In the present system, it is preferred to control density by control of the raw ore feed rate, because the feed rate is a relatively insensitive control parameter. Therefore relatively large step changes in feed rate will result in smaller variations in density, facilitating the control of the operation. However, as noted above, other operating parameters also affect density (such as flame temperature, air/fuel ratio, and air flow rate) and could be used for control if desired by suitable controllers 38 and circuitry.

What is claimed is:

1. In a perlite expansion process, an improved method for monitoring the density of the expanded perlite product, which method comprises:
    (a) passing a non-homogeneous, granular expanded perlite product through a conduit section of predetermined volume;
    (b) impinging penetrating radiation on one side of said conduit section while passing said expanded perlite product therethrough;
    (c) detecting on the other side of said conduit section at least a portion of the unabsorbed fraction of said penetrating radiation which passes through said conduit section and said expanded perlite product; and
    (d) obtaining a signal proportional to the density of said expanded perlite product by means of a predetermined correlation among mass flow rate of said expanded perlite product, conduit section volume, and detected amount of the unabsorbed fraction of the incident penetrating radiation.

2. An improved method as in claim 1 wherein said penetrating radiation comprises beta, gamma or X radiation.

3. An improved method as in claim 1 wherein said monitoring is conducted on a substantially continuous basis.

4. In a perlite expansion process, an improved method for monitoring and controlling the density of the expanded perlite product, which method comprises:
    (a) passing a non-homogeneous, granular expanded perlite product through a conduit section of predetermined volume;
    (b) impinging penetrating radiation on one side of said conduit section while passing said expanded perlite product therethrough;
    (c) detecting on the other side of said conduit section at least a portion of the unabsorbed fraction of said penetrating radiation which passes through said conduit section and said expanded perlite product;
    (d) obtaining a signal proportional to the density of said expanded perlite product by means of a predetermined correlation among mass flow rate of said expanded perlite product, conduit section volume, and detected amount of the unabsorbed fraction of the incident penetrating radiation; and
    (e) utilizing the signal obtained to control the density of the expanded perlite product.

5. An improved method as in claim 4, wherein said utilizing of step (e) comprises:
    (i) feeding the obtained signal to analysis and control means wherein the value of the proportional signal is compared to a predetermined standard value which is proportional to the desired perlite product density; and
    (ii) activating means to apply corrective regulation to the amount of unexpanded feed ore supplied to the expander when the value of the proportional signal fails to compare satisfactorily to the predetermined standard value.

6. An improved method as in claim 4 wherein said penetrating radiation comprises beta, gamma or X radiation.

7. An improved method as in claim 4 wherein said monitoring and control is conducted on a substantially continuous basis.

* * * * *

UNITED STATES PATENT AND TRADEMARK OFFICE
CERTIFICATE OF CORRECTION

PATENT NO. : 4,186,306

DATED : January 29, 1980

INVENTOR(S) : Carl George Necker et al

It is certified that error appears in the above-identified patent and that said Letters Patent are hereby corrected as shown below:

Column 2, line 28, "FIGURE" should be --figure-- line 50, omit hyphen

Column 3, line 33 "wells" should be --walls--

Signed and Sealed this

Twenty-second Day of July 1980

[SEAL]

Attest:

SIDNEY A. DIAMOND

Attesting Officer

Commissioner of Patents and Trademarks